United States Patent
Kim

(10) Patent No.: US 9,651,947 B2
(45) Date of Patent: May 16, 2017

(54) APPARATUS FOR SWITCHING DRIVING MODE OF VEHICLE AND METHOD THEREOF

(71) Applicant: LG ELECTRONICS INC., Seoul (KR)

(72) Inventor: Hyun Kim, Seoul (KR)

(73) Assignee: LG Electronics Inc., Seoul (KR)

(*) Notice: Subject to any disclaimer, the term of this patent is extended or adjusted under 35 U.S.C. 154(b) by 0 days.

(21) Appl. No.: 14/833,170

(22) Filed: Aug. 24, 2015

(65) Prior Publication Data
US 2016/0209840 A1    Jul. 21, 2016

(30) Foreign Application Priority Data
Jan. 20, 2015    (KR) .................. 10-2015-0009399

(51) Int. Cl.
   *G05D 1/00*      (2006.01)
   *A61B 5/18*      (2006.01)
   (Continued)

(52) U.S. Cl.
   CPC ............. *G05D 1/0061* (2013.01); *A61B 5/18* (2013.01); *B60W 50/082* (2013.01);
   (Continued)

(58) Field of Classification Search
   CPC ........ G05D 1/0061; G05D 2201/0213; B60W 50/082; B62D 1/286
   (Continued)

(56) References Cited

U.S. PATENT DOCUMENTS 6,178,365 B1 * 1/2001 Kawagoe ............... B62D 1/286
                                                       180/167
7,266,436 B2 * 9/2007 Shirato ................. B62D 1/286
                                                       348/148
(Continued)

FOREIGN PATENT DOCUMENTS

| JP | 10-329575 | 12/1998 |
|----|-----------|---------|
| JP | 2010-264829 | 11/2010 |
| KR | 10-2012-0058230 | 6/2012 |

OTHER PUBLICATIONS

International Search Report and Written Opinion in International Application No. PCT/KR2015/009179, mailed Nov. 26, 2015, 15 pages.

(Continued)

*Primary Examiner* — Krishnan Ramesh
(74) *Attorney, Agent, or Firm* — Fish & Richardson P.C.

(57) ABSTRACT

Systems and techniques are disclosed for switching a vehicle driving mode. A sensing unit senses a state of a driver of a vehicle configured to be driven automatically or manually. An intention detecting unit detects whether the driver intends to switch from an automatic driving mode to a manual driving mode based on the state of the driver. An operation detecting unit detects whether the driver is able to operate the vehicle in the manual driving mode based on the state of the driver. A driving state predicting unit predicts a driving state of the vehicle in the manual driving mode based on detecting that the driver is able to operate the vehicle in the manual driving mode. A control unit determines that the predicted driving state of the vehicle meets a preset condition and switches from the automatic to the manual driving mode.

22 Claims, 8 Drawing Sheets

(51) Int. Cl.
*B60W 50/08* (2012.01)
*B60W 50/10* (2012.01)
*B60W 50/00* (2006.01)

(52) U.S. Cl.
CPC .......... *B60W 50/10* (2013.01); *G05D 1/0088* (2013.01); *B60W 2050/0089* (2013.01); *B60W 2540/22* (2013.01); *B60W 2540/30* (2013.01); *Y02T 10/84* (2013.01)

(58) Field of Classification Search
USPC ...................................................... 701/23, 1
See application file for complete search history.

(56) References Cited

U.S. PATENT DOCUMENTS

| | | | | |
|---|---|---|---|---|
| 7,885,730 B2* | 2/2011 | Kaufmann | ........... | B60K 28/066 340/425.5 |
| 8,818,608 B2* | 8/2014 | Cullinane | ............ | B60W 30/00 701/117 |
| 8,838,323 B2* | 9/2014 | Matsunaga | ........... | B60W 30/10 701/28 |
| 9,008,887 B2* | 4/2015 | Kindo | ................ | B60W 30/143 701/23 |
| 2005/0240328 A1* | 10/2005 | Shirato | ................. | B62D 1/286 701/41 |
| 2005/0273215 A1* | 12/2005 | Kuge | ................. | B60T 8/17551 701/1 |
| 2010/0168998 A1* | 7/2010 | Matsunaga | ........... | B60W 30/10 701/532 |
| 2013/0131907 A1* | 5/2013 | Green | ................. | G05D 1/0055 701/23 |
| 2014/0018993 A1* | 1/2014 | Kindo | ................ | B60W 30/143 701/23 |
| 2014/0088814 A1* | 3/2014 | You | ...................... | G05D 1/0061 701/23 |
| 2014/0156134 A1* | 6/2014 | Cullinane | ............ | B60W 30/00 701/23 |
| 2014/0211319 A1 | 7/2014 | Park et al. | | |
| 2015/0120124 A1* | 4/2015 | Bartels | ................. | B60W 50/10 701/23 |
| 2015/0253772 A1* | 9/2015 | Solyom | ................ | G05D 1/0212 701/25 |
| 2016/0039428 A1* | 2/2016 | Odate | ................. | B60W 50/082 701/23 |
| 2016/0041553 A1* | 2/2016 | Sato | .................. | B60W 50/0098 701/23 |
| 2016/0121904 A1* | 5/2016 | Prakah-Asante | ..... | B60W 50/08 701/1 |
| 2016/0207536 A1* | 7/2016 | Yamaoka | ........... | B60W 30/182 |
| 2016/0207537 A1* | 7/2016 | Urano | ................. | B60W 30/182 |
| 2016/0207538 A1* | 7/2016 | Urano | ................. | B60W 30/182 |
| 2016/0209841 A1* | 7/2016 | Yamaoka | ............. | G05D 1/0088 |

OTHER PUBLICATIONS

Office Action issued in Korean Application No. 10-2015-0009399 on Jan. 14, 2016, 5 pages.

* cited by examiner

APPARATUS FOR SWITCHING DRIVING MODE OF VEHICLE AND METHOD THEREOF

CROSS-REFERENCE TO RELATED APPLICATION

Pursuant to 35 U.S.C. §119(a), this application claims the benefit of earlier filing date and right of priority to Korean Application No. 10-2015-0009399, filed on Jan. 20, 2015, the contents of which is incorporated by reference herein in its entirety.

BACKGROUND OF THE INVENTION

1. Field of the Invention

The present disclosure relates to an apparatus for switching a driving mode of a vehicle and a method thereof.

2. Background of the Invention

In general, an autonomous vehicle recognizes a road situation such as a neighbor vehicle, a pedestrian, an obstacle, a traffic lane, a traffic signal, and the like, through an advanced driving assist system (ADAS) attached thereto, and is automatically driven on the basis of the recognized information.

SUMMARY OF THE INVENTION

Therefore, an aspect of the detailed description has been made to solve the above-mentioned problems and other problems.

Another aspect of the detailed description is to provide an apparatus for switching a driving mode of a vehicle, capable of detecting a driver's intention to switch a vehicle to a manual driving mode, determining whether the vehicle can be safely operated in the manual driving mode, and determining whether to switch the vehicle to the manual driving mode, and a method thereof.

To achieve these and other advantages and in accordance with the purpose of this specification, as embodied and broadly described herein, an apparatus for switching a driving mode of a vehicle may include: a sensing configured to sense a state of a driver of a vehicle that can be driven automatically or manually; a mode switching intention detecting unit configured to detect a mode switching intention of the driver to switch a driving mode of the vehicle to a manual driving mode on the basis of the state of the driver sensed when the vehicle is in an automatic driving mode; an operation availability detecting unit configured to detect whether the driver is able to operate the vehicle in the manual driving mode, on the basis of the state of the driver sensed after the mode switching intention is detected; a driving state predicting unit configured to predict a driving state of the vehicle according to a possible driver's operation on the assumption that a driving mode of the vehicle is the manual driving mode for a preset period of time, on the basis of the fact that the driver is able to operate the vehicle in the manual driving mode; and a control unit configured to switch the driving mode of the vehicle to the manual driving mode, on the basis of the fact that the predicted driving state of the vehicle meets a preset condition.

In an exemplary embodiment of the present disclosure, the sensing unit may sense at least one of a position of at least one of both hands and both feet of the driver, the driver's posture, the driver's eyes, a degree of blinking of the driver, and a degree to which the driver's eyelids cover the eyes, as a state of the driver.

In an exemplary embodiment of the present disclosure, when the vehicle is in the automatic driving mode and it is sensed that at least one of both hands of the driver is holding the steering wheel, the mode switching intention detecting unit may detect the driver's mode switching intention.

In an exemplary embodiment of the present disclosure, in a preset situation in which the vehicle is in the automatic driving mode and a speed is required to be controlled, when it is sensed that least one of the driver's both feet is laid on an accelerator or a brake in response to the preset situation, the mode switching intention detecting unit may detect the driver's mode switching intention.

In an exemplary embodiment of the present disclosure, the apparatus may further include; a display unit configured to output an object corresponding to a driving mode of the vehicle.

In an exemplary embodiment of the present disclosure, after the mode switching intention is detected, when it is sensed that the driver's eyes are bent toward a preset object output on the display unit or a particular object recognized by an advanced driving assist system (ADAS), the operation availability detecting unit may detect that the driver is able to operate the vehicle in the manual driving mode.

In an exemplary embodiment of the present disclosure, the preset object may include an object for informing the driver about a dangerous situation around the vehicle when the vehicle is operated in the manual driving mode.

In an exemplary embodiment of the present disclosure, after the mode switching intention is detected, when a degree to which the driver's eyes gaze at a driving route of the vehicle meets a preset degree, the operation availability detecting unit may determine that the driver is able to operate the vehicle in the manual driving mode.

In an exemplary embodiment of the present disclosure, the operation availability detecting unit may calculate a degree of fatigue of the driver on the basis of a degree of the driver's blinking and a degree to which the driver's eyelids cover the eyes sensed after the mode switching intention is detected, and when the calculated degree of fatigue of the driver meets a preset degree, the operation availability detecting unit may detect that the driver is able to operate the vehicle in the manual driving mode.

In an exemplary embodiment of the present disclosure, when the predicted driving state of the vehicle does not meet the preset condition, the control unit may maintain the driving mode of the vehicle in the automatic driving mode.

To achieve these and other advantages and in accordance with the purpose of this specification, as embodied and broadly described herein, a method for switching a driving mode of a vehicle which can be driven automatically and manually, may include: (a) detecting a mode switching intention of the driver to switch a driving mode of the vehicle to a manual driving mode on the basis of the state of the driver sensed when the vehicle is in an automatic driving mode; (b) detecting whether the driver is able to operate the vehicle in the manual driving mode, on the basis of the state of the driver sensed after the mode switching intention is detected; (c) predicting a driving state of the vehicle according to a possible driver's operation on the assumption that a driving mode of the vehicle is the manual driving mode for a preset period of time, on the basis of the fact that the driver is able to operate the vehicle in the manual driving mode; and (d) switching the driving mode of the vehicle to the manual driving mode, on the basis of the fact that the predicted driving state of the vehicle meets a preset condition.

In an exemplary embodiment of the present disclosure, (a) and (b) each may include sensing at least one of a position of at least one of both hands and both feet of the driver, the driver's posture, the driver's eyes, a degree of blinking of the driver, and a degree to which the driver's eyelids cover the eyes, as a state of the driver.

In an exemplary embodiment of the present disclosure, (a) may include when the vehicle is in the automatic driving mode and it is sensed that at least one of both hands of the driver is holding the steering wheel, detecting the driver's mode switching intention.

In an exemplary embodiment of the present disclosure, (a) may include: detecting the driver's mode switching intention, when it is sensed that least one of the driver's both feet is laid on an accelerator or a brake in response to the preset situation in a preset situation in which the vehicle is in the automatic driving mode and a speed is required to be controlled.

In an exemplary embodiment of the present disclosure, the vehicle may include a display unit configured to output an object corresponding to a driving mode of the vehicle.

In an exemplary embodiment of the present disclosure, (b) may include: after the mode switching intention is detected, when it is sensed that the driver's eyes are bent toward a preset object output on the display unit or a particular object recognized by an advanced driving assist system (ADAS), detecting that the driver is able to operate the vehicle in the manual driving mode.

In an exemplary embodiment of the present disclosure, the preset object may include an object for informing the driver about a dangerous situation around the vehicle when the vehicle is operated in the manual driving mode.

In an exemplary embodiment of the present disclosure, (b) may include: after the mode switching intention is detected, when a degree to which the driver's eyes gaze at a driving route of the vehicle meets a preset degree, determining that the driver is able to operate the vehicle in the manual driving mode.

In an exemplary embodiment of the present disclosure, (b) may include: calculating a degree of fatigue of the driver on the basis of a degree of the driver's blinking and a degree to which the driver's eyelids cover the eyes sensed after the mode switching intention is detected, and when the calculated degree of fatigue of the driver meets a preset degree, detecting that the driver is able to operate the vehicle in the manual driving mode.

In an exemplary embodiment of the present disclosure, (d) may include: when the predicted driving state of the vehicle does not meet the preset condition, maintaining the driving mode of the vehicle in the automatic driving mode.

Further scope of applicability of the present application will become more apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from the detailed description.

BRIEF DESCRIPTION OF THE DRAWINGS

The accompanying drawings, which are included to provide a further understanding of the invention and are incorporated in and constitute a part of this specification, illustrate exemplary embodiments and together with the description serve to explain the principles of the invention.

In the drawings.

DETAILED DESCRIPTION OF THE INVENTION

The terminology used herein is for the purpose of describing particular embodiments only and is not intended to be limiting of the invention. Unless otherwise defined, all terms used herein have the same meaning as commonly understood by one of ordinary skill in the art to which this invention pertains, and should not be interpreted as having an excessively comprehensive meaning nor as having an excessively contracted meaning. If technical terms used herein is erroneous that fails to accurately express the technical idea of the present invention, it should be replaced with technical terms that allow the person in the art to properly understand. The general terms used herein should be interpreted according to the definitions in the dictionary or in the context and should not be interpreted as an excessively contracted meaning.

As used herein, the singular forms "a", "an" and "the" are intended to include the plural forms as well, unless the context clearly indicates otherwise. It will be further understood that the terms "comprises" "comprising," "includes" and/or "including" when used herein, specify the presence of stated features, integers, steps, operations, elements, and/or components, but do not preclude the presence or addition of one or more other features, steps, operations, elements, components, and/or groups thereof.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present invention.

The exemplary embodiments of the present invention will now be described with reference to the accompanying drawings, in which like numbers refer to like elements throughout.

In describing the present invention, if a detailed explanation for a related known function or construction is considered to unnecessarily divert the gist of the present invention, such explanation has been omitted but would be understood by those skilled in the art. The accompanying drawings of the present invention aim to facilitate understanding of the present invention and should not be construed as limited to the accompanying drawings. The technical idea of the present invention should be interpreted to embrace all such alterations, modifications, and variations in addition to the accompanying drawings.

Figure 1:
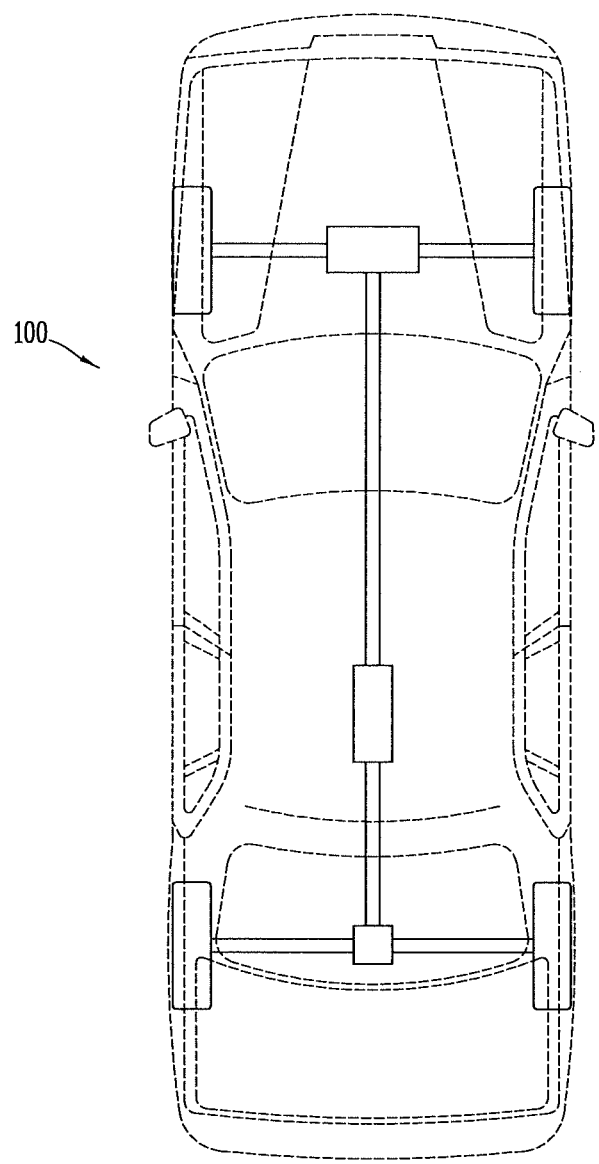
FIG. 1 is a schematic view illustrating a vehicle according to an exemplary embodiment of the present disclosure.

FIG. 1 is a schematic view of a vehicle (for example, an electric vehicle) illustrating an exemplary embodiment of the present disclosure.

The embodiment of the present invention may also be applied to pure electric vehicles, hybrid electric vehicles (HEV), and the like, as well as to general vehicles (gasoline vehicles, gas vehicles, and the like). The hybrid electric vehicles (HEV) include a battery pack composed of a plurality of battery cells for receiving required power. The plurality of battery cells included in the battery pack need to have a uniform voltage, respectively, in order to obtain stability, improve a life span, and obtain a high output.

Figure 2:
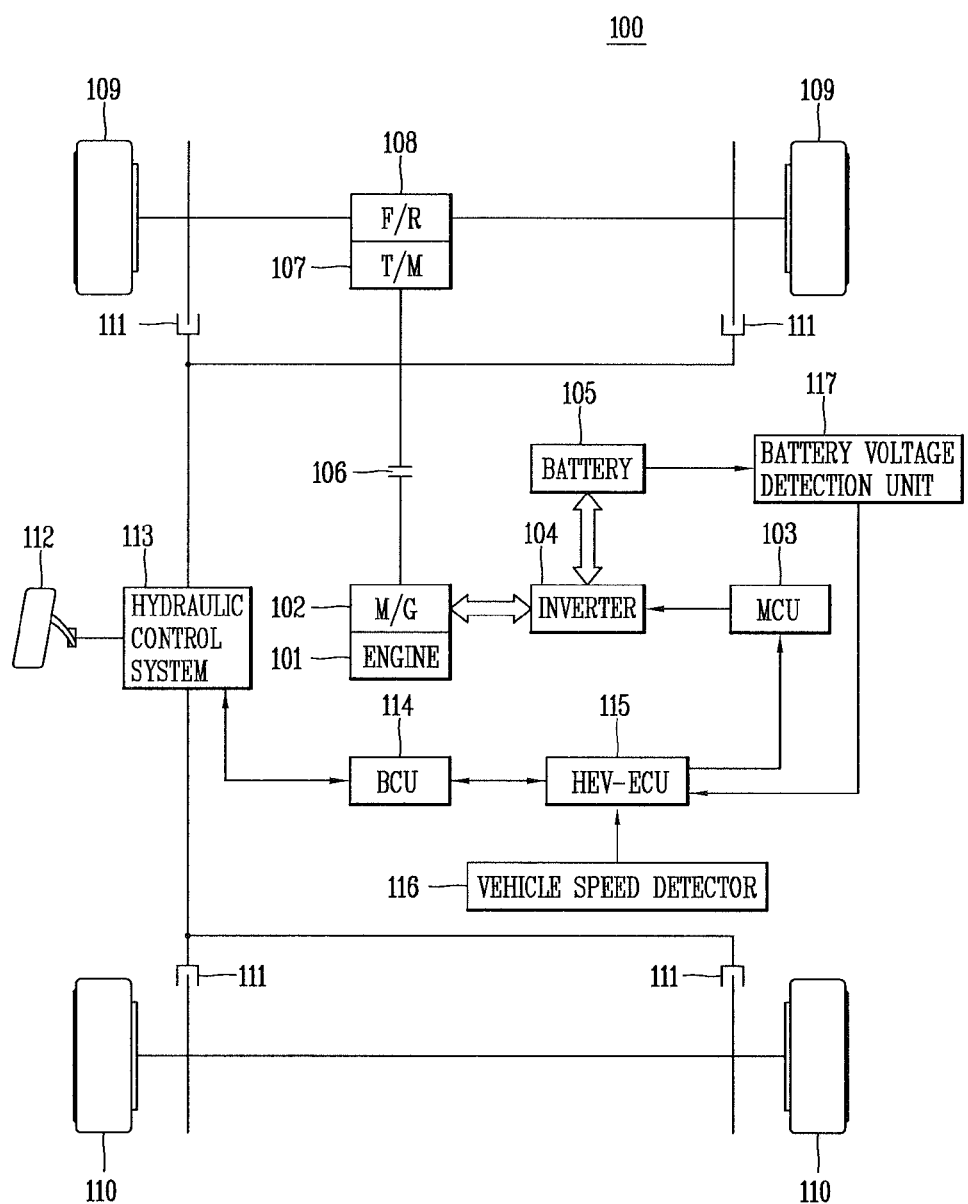
FIG. 2 is a block diagram illustrating a configuration of a vehicle according to an exemplary embodiment of the present disclosure.

FIG. 2 is a view illustrating a configuration of a vehicle (for example, an HEV) illustrating an exemplary embodiment of the present disclosure.

As illustrated in FIG. 2, a vehicle 100 illustrating an exemplary embodiment of the present disclosure includes an engine 101 and a motor/generator unit (M/G unit) as power sources. Driven wheels driven by the power sources include front wheels in a front-wheel drive vehicle and rear wheels in a rear wheel drive vehicle. Hereinafter, the front wheel drive vehicle will be described. An embodiment of the rear wheel drive vehicle will be obvious from the following descriptions of the front wheel drive vehicle.

The M/G unit 102 is a device selectively serving as a motor or a generator according to a driving state, which is obvious to the skilled person in the art. Thus, in the following descriptions, for the sake of understanding, the M/G unit 102 may be used as the same title of the motor or the generator, and all of them designate the same element. The engine 101 and the motor 102 of the electric vehicle are connected in series to a transmission.

Also, the M/G unit 102 is driven by a signal from an inverter 104 under the control of a motor control unit (MCU) 103.

The inverter 104 drives the M/G unit 102 as a power source by using electric energy stored in the battery 105 under the control of the MCU 103, and when the inverter 104 drives the M/G unit 102 as a generator, the inverter 104 charges electric energy generated by the M/G unit 102 to the battery 105.

Power of the engine 101 and the M/G unit 102 is transferred to the transmission (T/M) 107 through a clutch 106, and transferred to front wheels 109 through a final drive gear (F/R) 108. Rear wheels 110 are non-driven wheels that are not driven by the engine 101 and the M/G unit 102.

A wheel brake apparatus 111 is installed at the front wheels 109 and the rear wheels 110 in order to reduce a rotation speed of the wheels. The electric vehicle includes a brake pedal 112 and a hydraulic control system 113 for hydraulically controlling each wheel brake apparatus 111 based on oil pressure generated according to manipulation of the brake pedal 112, in order to drive each wheel brake apparatus 111. The electric vehicle includes a brake control unit (BCU) 114 for controlling the hydraulic control system 113 and receiving a brake control state from the hydraulic control system 113.

When a driver manipulates the brake pedal 112, the BCU 114 detects oil pressure generated from the hydraulic control system 113. The BCU 114 calculates a braking force to be applied to the driven wheels (e.g., the front wheels 109), a hydraulic braking force to be braked by oil pressure, and a regenerative braking force to be braked by regenerative braking based on the detected oil pressure. Accordingly, the BCU 114 supplies the calculated hydraulic braking force to the wheel brake apparatus 111 of the front wheels 109 under the control of the hydraulic control system 113.

The electric vehicle includes a hybrid electric vehicle-electronic control unit (HEV-ECU) 115 communicating with the BCU 114 and the MCU 103 to control them to realize an electric vehicle that performs a maximum speed limiting method.

The regenerative braking force calculated by the BCU 114 is transferred to the REV-ECU 115, and the HEV-ECU 115 controls the MCU 103 on the basis of the received regenerative braking force. Accordingly, the MCU 103 drives the M/G unit 102 as a generator such that the regenerative braking force designated by the HEV-ECU 115 can be realized. Here, electric energy generated by the M/G unit 102 is stored in the battery 105.

The electric vehicle further includes a vehicle speed detector 116 for detecting a vehicle speed.

The HEV-ECU 115 utilizes the vehicle speed detected by the vehicle speed detector 116 as data for controlling the BCU 114 and the MCU 103.

Also, the electric vehicle further includes a battery voltage detecting unit 117 for detecting a voltage of the battery 105. The battery voltage detecting unit 117 detects the current voltage of the battery 105 and provides result data to allow the HEV-ECU 115 to limit a maximum speed of the electric vehicle according to a variations of the detected current voltage and a pre-set reference voltage.

Hereinafter, a configuration of a telematics terminal 200 illustrating an exemplary embodiment of the present disclosure will be described with reference to FIG. 3.

Figure 3:
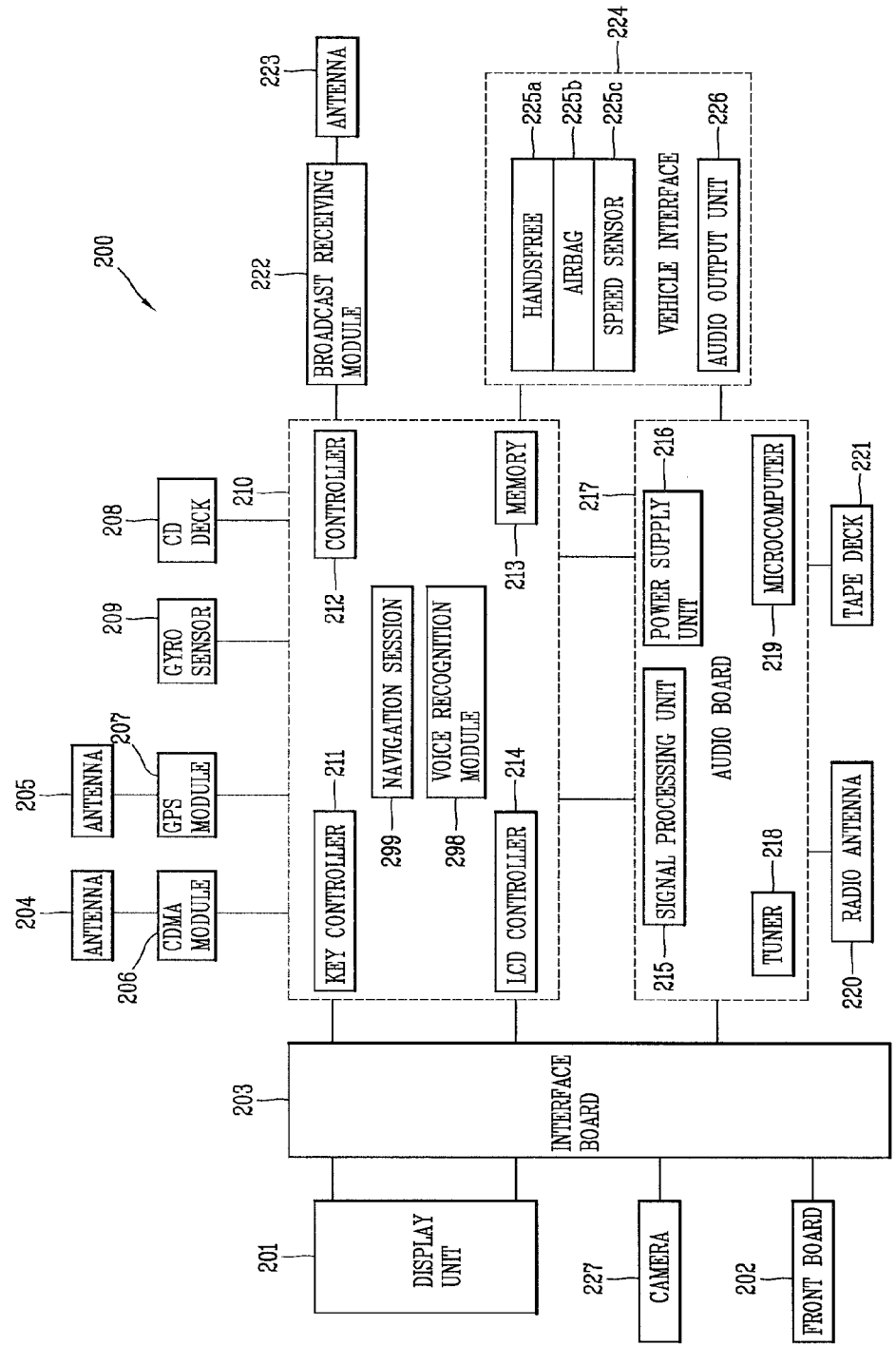
FIG. 3 is a block diagram illustrating a configuration of a telematics terminal according to an exemplary embodiment of the present disclosure.

As illustrated in FIG. 3, the telematics terminal 200 includes a main board 210 including a control unit (e.g., a central processing unit (CPU)) 212 for controlling the telematics terminal 200 on the whole, a memory 213 for storing various types of information, a key control unit 211 for controlling various key signals, and a liquid crystal display (LCD) control unit 214 for controlling an LCD.

The memory 213 stores map information (map data) for displaying road guidance information on a digital map. Also, the memory 213 stores a traffic information collecting control algorithm for inputting traffic information according to the situation of a road in which the vehicle currently travels (runs), and information for controlling the algorithm.

The main board 210 includes a code division multiple access (CDMA) module 206, i.e., a mobile communication terminal having a unique device number as assigned and installed in the vehicle, a global position system (GPS) module 207 for guiding a location of the vehicle, receiving a GPS signal for tracking a travel route from a start point to a destination, or transmitting traffic information collected by the user, as a GPS signal, a CD deck 208 for reproducing a signal recorded in a CD (Compact Disk), a gyro sensor 209, and the like. The CDMA module 206 and the GPS module 207 transmit or receive signals via antennas 204 and 205.

A broadcast receiving module 222 is connected with the main board 210 and receives a broadcast signal via an antenna 223. A display unit (i.e., an LCD) 201 under the control of the LCD control unit 214, a front board 202 under the control of the key control unit 211, and a camera 227 for capturing the interior and/or the exterior of a vehicle are connected to the main board 210 via an interface board 203. The display unit 201 displays various video signals and character signals, and the front board 202 includes buttons for various key signal inputs and provides a key signal corresponding to a button selected by the user to the main board 210. Also, the display unit 201 includes a proximity sensor and a touch sensor (touch screen) of FIG. 2.

The front board 202 includes a menu key for directly inputting traffic information. The menu key may be configured to be controlled by the key control unit 211.

An audio board 217 is connected with the main board 210 and processes various audio signals. The audio board 217 includes a microcomputer 219 for controlling the audio board 217, a tuner 218 for receiving a radio signal, a power source unit 216 for supplying power to the microcomputer 219, and a signal processing unit 215 for processing various voice signals.

The audio board 217 also includes a radio antenna 220 for receiving a radio signal and a CD deck 221 for reproducing an audio signal of a compact disc (CD). The audio board 217 may further include a voice output unit (e.g., an amplifier) 226 for outputting a voice signal processed by the audio board 217.

The voice output unit (amplifier) 226 is connected to a vehicle interface 224. Namely, the audio board 217 and the main board 210 are connected to the vehicle interface 224. A handsfree 225a for inputting a voice signal, an airbag 225b configured for the security of a passenger, a speed sensor 225c for detecting a speed of the vehicle, and the like, may be connected to the vehicle interface 224. The speed sensor 225c calculates a vehicle speed and provides the calculated vehicle speed information to the CPU 212.

The navigation session 300 applied to the telematics ten final 200 generates road guidance information on the basis of the map data and current location information of the vehicle and provides the generated road guidance information to a user.

The display unit 201 detects a proximity touch within a display window via a proximity sensor. For example, when a pointer (e.g., user's finger or a stylus) is proximity-touched, the display unit 201 detects the position of the proximity touch and outputs position information corresponding to the detected position to the control unit 212.

A voice recognition device (or a voice recognition module) 301 recognizes a voice pronounced by the user and performs a corresponding function according to the recognized voice signal.

The navigation session 300 applied to the telematics terminal 200 displays a travel route on map data, and when the location of the mobile terminal 100 is within a pre-set distance from a blind spot included in the travel route, the navigation session 300 automatically forms a wireless network with a terminal mounted in an adjacent vehicle (e.g., a vehicle navigation device) and/or a mobile communication terminal carried by a nearby pedestrian through wireless communication (e.g., a short-range wireless communication network), to receive location information of the adjacent vehicle from the terminal mounted in the adjacent vehicle and receive location information of the nearby pedestrian from the mobile communication terminal carried by the nearby pedestrian.

An apparatus for switching a driving mode of a vehicle according to an exemplary embodiment of the present disclosure may be applied to an automatic driving system according to the related art or may be applied to the telematics terminal 200 (or a head up display (HUD)) and a vehicle dashboard (or an instrument cluster). The related art automatic driving system is disclosed in U.S. Pat. No. 8,825,258, and thus, detailed descriptions thereof will be omitted.

Meanwhile, if a driver, who has not adapted himself or herself enough for road situations, the current driving speed, and the like, immediately switches an automatic driving mode to a manual driving mode, a traffic accident may occur due to poor driving operation, or the like.

Thus, an apparatus and method whereby when a driver's intention for switching a mode of a vehicle from an automatic driving mode to a manual driving mode is detected, a preparation state of the driver, such as whether the driver has adapted himself or herself for road situations, the current driving speed, and the like, is recognized, and thereafter, the automatic driving mode of the vehicle is switched to a manual driving mode so that the driver may safely drive in the manual driving mode will be described.

Figure 4:
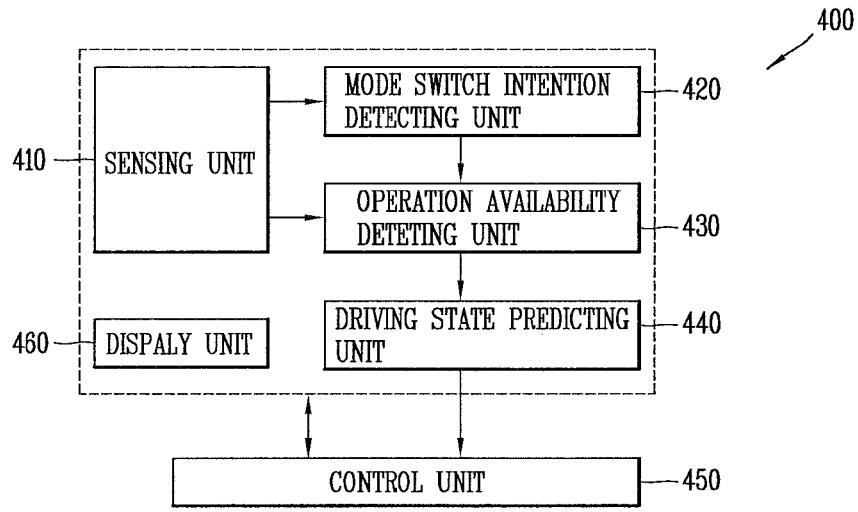
FIG. 4 is a block diagram illustrating a configuration of an apparatus for switching a driving mode of a vehicle according to an exemplary embodiment of the present disclosure.

FIG. 4 is a block diagram illustrating a configuration of an apparatus for switching a driving mode of a vehicle related to an exemplary embodiment of the present disclosure.

Referring to FIG. 4, an apparatus 400 for switching a driving mode of a vehicle according to an exemplary embodiment of the present disclosure may include a sensing unit 410, a mode switching intention detecting unit 420, an operation availability detecting unit 430, a driving state predicting unit 440, a control unit 450, and a display unit 460.

First, the sensing unit 410 may sense a state of a driver of a vehicle that may be driven automatically and manually. A state of the vehicle driver may be defined by a position or a movement of a preset body portion with respect to the driver.

In an exemplary embodiment, the sensing unit 410 may sense at least one of a position of at least one of both hands and both feet of the driver, the driver's posture, the driver's eyes, a degree of blinking of the driver, and a degree to which the driver's eyelids cover the eyes, as a state of the driver.

To this end, the sensing unit 410 may be configured as a camera for capturing an image of the driver's body and capture images of the driver's both hands, both feet, posture, eyes, and the like. Alternatively, the sensing unit 410 may be disposed as a touch sensor in a steering wheel of the vehicle to sense at least one of both hands laid on the steering wheel.

In another exemplary embodiment, the sensing unit 410 may include a driver state monitoring (DSM) system capable of detecting the driver's blinking, a direction of the driver's eyes, and the like, in real time.

The mode switching intention detecting unit 420 may detect the driver's mode switching intention to switch a driving mode of the vehicle to a manual driving mode, on the basis of a state of the driver sensed when the vehicle is in an automatic driving mode.

In an exemplary embodiment, when it is sensed that at least one of the driver's both hands holds the steering wheel of the vehicle in the automatic driving mode of the vehicle, the mode switching intention detecting unit 420 may detect the driver's mode switching intention.

In another exemplary embodiment, in case of a preset situation in which the vehicle is in the automatic driving mode and a speed is required to be controlled, when it is sensed that at least one of the driver's both feet is laid on an accelerator or a brake in response to the preset situation, the mode switching intention detecting unit 420 may detect the driver's mode switching intention.

In detail, the situation in which a speed is required to be controlled may be set to a case in which a stop signal is generated, a case in which the vehicle is driving on the curves, a case in which there is an obstacle is present on the road, a case in which there is a vehicle driving nearby.

In detail, while the vehicle is driving at a speed equal to or higher than a preset speed, when a dangerous object is sensed in front of the vehicle and at least one of the driver's feet is sensed to be laid on the brake, the mode switching intention detecting unit 420 may detect the driver's mode switching intention.

Alternatively, while the vehicle is driving on the express way, when at least one of the driver's feet is sensed to be laid on the accelerator, the mode switching intention detecting unit 420 may detect the driver's mode switching intention.

The display unit 460 may output an object corresponding to a driving mode of the vehicle, and may be formed as a liquid crystal display (LCD), a thin film transistor liquid crystal display (TFT-LCD), an organic light emitting diode, a flexible display, a 3D display, and the like.

For example, an icon corresponding to the automatic driving mode, the current driving mode of the vehicle, may be output on the display 460. Similarly, when the driving mode of the vehicle is switched, an icon corresponding to the manual driving mode may be output on the display 460.

On the basis of a state of the driver sensed after the mode switching intention is detected, the operation availability detecting unit 430 may detect whether the driver may operate the vehicle in the manual driving mode.

In detail, when the driver's mode switching intention is detected by the mode switching intention detecting unit 420, the sensing unit 410 senses a position or a movement of a preset body portion with respect to the driver, again. Subsequently, on the basis of the sensing result, the operation availability detecting unit 430 may detect whether the driver may be able to safely operate the vehicle in the manual driving mode.

In an exemplary embodiment, after the mode switching intention is detected, when it is sensed that the driver's eyes are bent toward a particular object recognized by an advanced driving assist system (ADAS) the operation availability detecting unit 430 may detect that the driver may be able to operate the vehicle in the manual driving mode.

To this end, the sensing unit 410 may include a driver state monitoring (DSM) system capable of detecting the driver's blinking, a direction of the driver's eyes, and the like, in real time.

Also, a pre-set object output on the display unit 460 may include an object for informing about a dangerous situation around the vehicle when the vehicle operates in the manual driving mode. For Example, the preset object may be an alarm notification or a message output on a dashboard or a display unit.

In detail, after the mode switching intention is detected, the operation availability detecting unit 430 may receive driver's eyes information recognized by the DSM system from the DSM system through a wired network or a wireless network.

Accordingly, when a direction of the driver's eyes recognized by the DSM system is analyzed to be bent toward the alarm notification or message output on the display unit 460, the operation availability detecting unit 430 may detect that the driver may be able to operate the vehicle in the manual driving mode.

In another specific exemplary embodiment, the operation availability detecting unit 430 may receive object information (particular object) corresponding to a neighbor vehicle, a pedestrian, an obstacle, a traffic lane, a traffic signal, and the like, recognized the ADAS from the ADAS through a wired network or a wireless network.

Accordingly, when a direction of the driver's eyes recognized by the DSM system is analyzed to be bent toward the particular object recognized by the ADAS, the operation availability detecting unit 430 may detect that the driver may be able to operate the vehicle in the manual driving mode.

In another exemplary embodiment, after the mode switching intention is detected, when a degree to which the driver keeps his or her eyes on a driving route meets a preset degree, the operation availability detecting unit 430 may detect that the driver may be able to operate the vehicle in the manual driving mode.

In detail, as described above, after the mode switching intention is detected, the operation availability detecting unit 430 may receive driver's eyes information recognized by the DSM system from the DSM system through a wired network or a wireless network.

Accordingly, when it is analyzed that the driver keeps his or her eyes on the driving route of the vehicle for more than a preset period of time as recognized by the DSM system, the operation availability detecting unit 430 may detect that the driver may be able to operate the vehicle in the manual driving mode. That is, on the basis of whether the driver keeps his or her eyes on the driving route of the vehicle for more than a preset period of time, a degree of the driver's carelessness may be analyzed.

In another exemplary embodiment, on the basis of a degree to which the driver blinks or a degree to which the driver's eyelids cover the driver's eyes sensed after the mode switching intention is detected, the operation availability detecting unit 430 calculates a degree of fatigue of the driver, and when the calculated degree of fatigue of the driver meets a preset degree, the operation availability detecting unit 430 may detect that the driver may be able to operate the vehicle in the manual driving mode.

In detail, as described above, after the mode switching intention is detected, the operation availability detecting unit 430 may receive the driver's eyes information recognized by the DSM system from the DSM system through a wired network or a wireless network.

Accordingly, the operation availability detecting unit 430 may calculate a degree of fatigue on the basis of the number of times of the driver's blinking and a degree to which the driver's eyelids cover the driver's eyes recognized by the DSM system. On the basis of the calculated degree of fatigue, the operation availability detecting unit 430 may determine whether the driver drowses, or the like, and when the calculated degree of the driver meets a preset degree, the operation availability detecting unit 430 may detect that the driver may be able to operate the vehicle in the manual driving mode.

On the basis of the fact that the driver is able to operate the vehicle in the manual driving mode, the driving state predicting unit 440 may predict a driving state of the vehicle according to a driver's operation that may be input on the assumption that the driving mode of the vehicle is the manual driving mode for a preset period of time.

That is, in this case, the driving mode of the vehicle is not actually switched to the manual driving mode, but a driving state of the vehicle on the assumption that the vehicle is operated through driver's inputting such as the driver's operation of the handle, brake, or accelerator for a preset period of time is predicted.

When the predicted driving state of the vehicle meets a preset condition, the control unit 450 may switch the driving mode of the vehicle to the manual driving mode.

In detail, when the vehicle is not interfered with by a neighbor vehicle, a pedestrian, an obstacle, and the like, and the vehicle is operated, while keeping its lane and observing traffic signals according to the predicted driving state of the vehicle, the control unit may switch the driving mode of the vehicle to the manual driving mode.

In another exemplary embodiment, when the driving state of the vehicle does not meet the preset condition, the control unit 450 may maintain the driving mode of the vehicle in the automatic driving mode.

Also, the control unit 450 may control a general operation of the mode switching intention detecting unit 420, the operation availability detecting unit 430, a driving state predicting unit 440, and the display unit 460.

Figure 5:
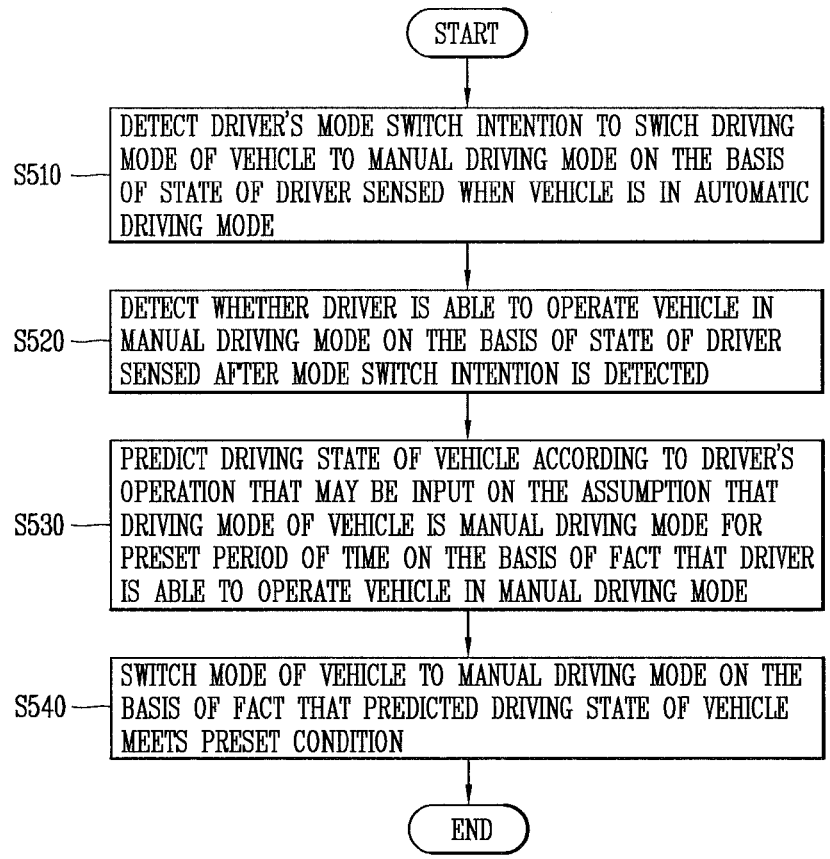
FIG. 5 is a flow chart illustrating a method for switching a driving mode of a vehicle according to an exemplary embodiment of the present disclosure.

FIG. 5 is a flow chart illustrating a method for switching a driving mode of a vehicle according to an exemplary embodiment of the present disclosure.

Referring to FIG. 5, on the basis of a state of the driver sensed when the vehicle is in the automatic driving mode, a driver's mode switching intention to switch the driving mode of the vehicle to the manual driving mode is detected in step S510.

In an exemplary embodiment, prior to step S510, it may be first determined whether the vehicle is in the automatic driving mode and whether the vehicle is driving on the road in which a manual operation is available. Thus, when the vehicle is driving in the automatic driving mode on the road in which a manual operation is available, step S510 may be performed.

Thereafter, when it is detected that the driver is able to operate the vehicle in the manual driving mode, a driving state of the vehicle according to a possible driver's operation on the assumption that the driving mode of the vehicle is the manual driving mode for a predetermined period of time is predicted in step S530.

Thereafter, when the predicted driving state of the vehicle meets a preset condition, the driving mode of the vehicle is switched to the manual driving mode in step S540.

Hereinafter, each of described in FIG. 5 will be described in more detail.

Figure 6:
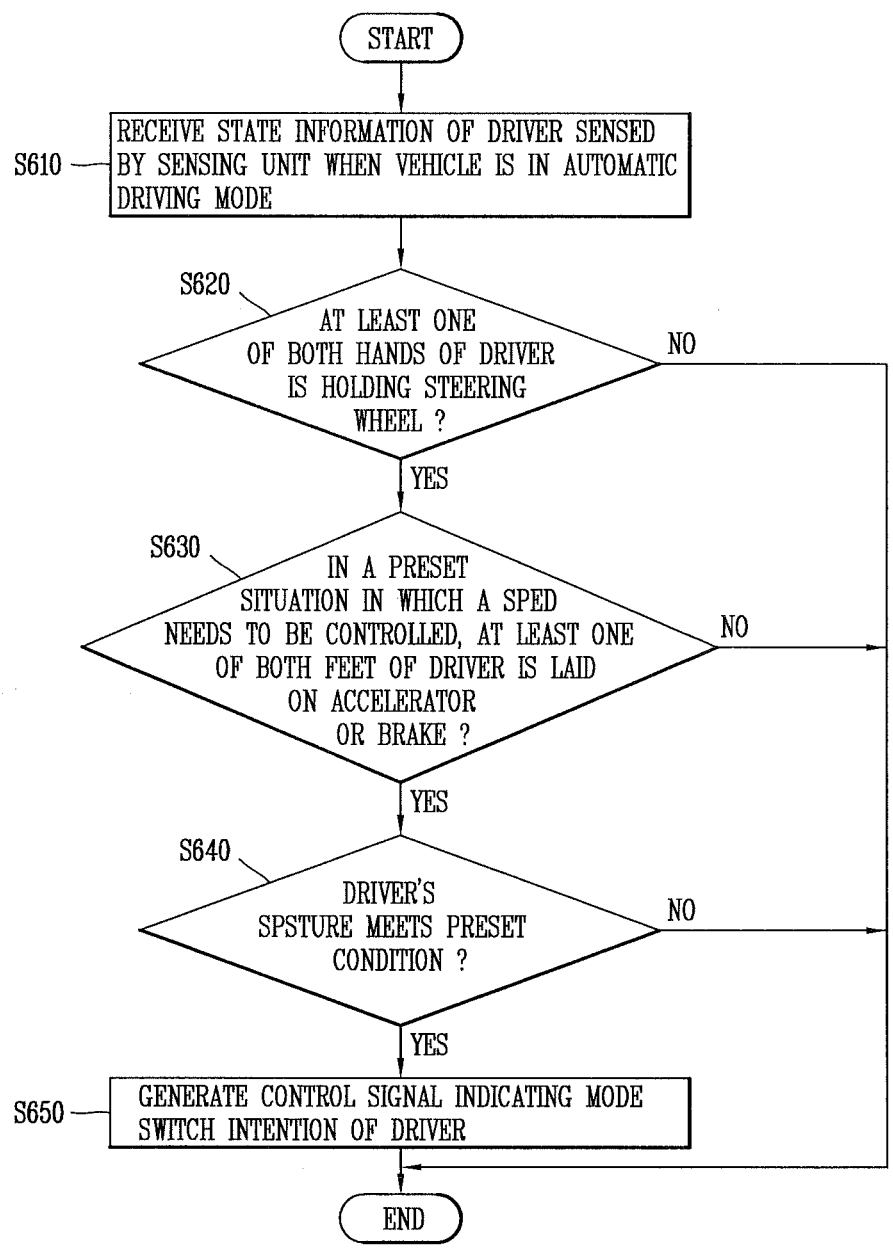
FIG. 6 is a flow chart illustrating an embodiment of detecting a driver's mode switching intention.

FIG. 6 is a flow chart illustrating an embodiment of detecting a driver's mode switching intention.

That is, FIG. 6 is a specific embodiment of step S510 of FIG. 5 and each step thereof is executed by the mode switching intention detecting unit 420.

Referring to FIG. 6, when the vehicle is in the automatic driving mode, state information of the driver sensed by the sensing unit 410 is received in step S610.

In an exemplary embodiment, the sensing unit 410 may sense at least one of a position of at least one of both hands and both feet of the driver, the driver's posture, the driver's eyes, a degree of blinking of the driver, and a degree to which the eyelids cover the eyes, as a state of the driver.

To this end, the sensing unit 410 may include a camera, a touch sensor, a driver state monitoring (DSM) system, and the like.

In detail, the camera may capture images of the drive's both hands, both feet, posture, eyes, and the like, or the touch disposed in the steering wheel of the vehicle may sense that at least one of the driver's both hands is laid on the steering wheel of the vehicle. In another exemplary embodiment, the sensing unit 410 may detect the driver's blinking, the driver's eyes direction, and the like, by using the DSM system.

Thereafter, it is determined whether at least one of the driver's both hands is holding the steering wheel of the vehicle in step S620.

When it is determined that at least one of the driver's both hands is holding the steering wheel of the vehicle in step S620 and when a situation is a preset situation in which the vehicle is in the automatic driving mode and a speed is required to be controlled, it is determined whether at least one of the driver's both feet is laid on the accelerator or the brake in response to the preset situation in step S630.

In detail, the situation in which a speed is required to be controlled may be set to a case in which a stop signal is generated, a case in which the vehicle is driving on the curves, a case in which there is an obstacle is present on the road, a case in which there is a vehicle driving nearby.

In an exemplary embodiment, while the vehicle is driving at a speed equal to or higher than a preset speed, when a dangerous object is sensed in front of the vehicle, it may be determined whether at least one of the driver's feet is laid on the brake.

In another exemplary embodiment, while the vehicle is driving on the express way, it may be determined whether at least one of the driver's feet is laid on the accelerator.

In step S630, it is determined that at least one of the driver's feet is laid on the accelerator or the brake according to a preset situation, it is determined whether a driver's posture meets a preset conditions in step S640.

In an exemplary embodiment, whether the driver sits straight up on the basis of an image captured by the camera.

When it is determined that the driver's posture meets a preset condition in step S640, a mode switching intention to switch the driving mode of the vehicle to the manual driving mode is detected from the driver. Accordingly, the mode switching intention detecting unit 420 generates a corresponding control signal in step S650.

The flow chart of FIG. 6 is an embodiment in which at least one of steps S620, S630, and S640 may be performed or the steps S620, S630, and S640 may be performed in predetermined order.

Also, even when only some of the steps are met, the drive's mode switching intention may be detected. For example, even when one of the driver's both hands holds the steering wheel (step S620), the driver's mode switching intention may be detected.

In another exemplary embodiment, a step for detecting the mode switching intention may be added.

Figure 7:
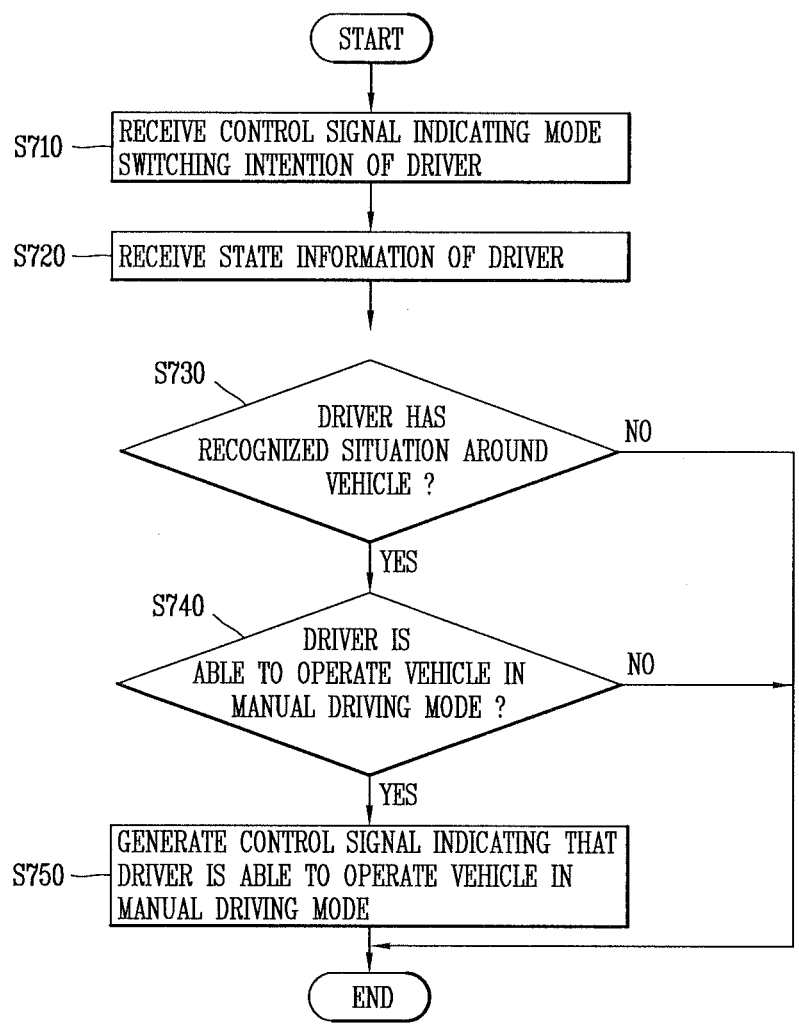
FIG. 7 is a flow chart illustrating an embodiment of detecting a driver is able to drive a vehicle in a manual driving mode.

FIG. 7 is a flow chart illustrating an embodiment of detecting whether the driver is able to operate the vehicle in the manual driving mode.

That is, FIG. 7 is a specific embodiment of step S520 of FIG. 5, and each step is executed by the operation availability detecting unit 430.

Referring to FIG. 7, first, a control signal corresponding to the driver's mode switching intention generated by the mode switching intention detecting unit 420 in step S650 of FIG. 6 is received in step S710.

Thereafter, state information of the driver sensed by the sensing unit 410 is received in step S720. In an exemplary embodiment, the sensing unit 410 may include a DSM system, and the operation availability detecting unit 430 may receive driver's eyes information recognized by the DSM system from the DSM system through a wired network or a wireless network.

Thereafter, it is determined whether the driver has recognized a situation around the vehicle in step S730.

In an exemplary embodiment, the operation availability detecting unit 430 may determine whether a direction of the driver's eyes recognized by the DSM system are bent toward the alarm notification or message output on the display unit 460 or the dashboard.

In another exemplary embodiment, the operation availability detecting unit 430 may receive object information (particular object) corresponding to a neighbor vehicle, a pedestrian, an obstacle, a traffic lane, a traffic signal, and the like, recognized the ADAS from the ADAS through a wired network or a wireless network.

Accordingly, the operation availability detecting unit 430 may determine whether a direction of the driver's eyes recognized by the DSM system is bent toward the particular object recognized by the ADAS.

When it is determined that the driver has recognized a situation around the vehicle in step S730, the driver's power of attention and a degree of fatigue are analyzed to determine whether the driver may be able to operate the vehicle in the manual driving mode in step S740. That is, it is determined whether the vehicle may be stably operated by the driver even when the vehicle is switched to the manual driving mode.

In an exemplary embodiment, the when it is analyzed that the driver's eyes recognized by the DSM system gaze at a driving route of the vehicle for more than a preset period of time, the operation availability detecting unit 430 may determine that the driver is able to operate the vehicle in the manual driving mode. That is, a degree of the power of attention (carelessness) of the driver is analyzed, and whether the driver is able to operate the vehicle in the manual driving mode is determined on the basis of the analyzed degree of the power of attention (carelessness).

In another exemplary embodiment, the operation availability detecting unit 430 may calculate the degree of the driver on the basis of the number of times of driver's blinking, a degree to which the driver's eye lids cover the eyes (the iris or the pupil), a time during which the driver's eye lids cover the eyes, and the like, recognized by the DSM system.

On the basis of the calculated degree of fatigue, the operation availability detecting unit 430 may determine whether the driver drowses, and when the calculated degree of driver's fatigue meets a preset degree, the operation availability detecting unit 430 may determine that the driver is able to operate the vehicle in the manual driving mode.

When it is determined that the driver is able to operate the vehicle in the manual driving mode in step S740, the operation availability detecting unit 430 generates a corresponding control signal in step S750.

The flow chart of FIG. 7 is an embodiment of the present disclosure, in which steps S730 and S74 may be simultaneously performed or step S740 may be performed first.

Also, even when only one of the steps is met, it may be determined that the driver is able to operate the vehicle in the manual mode. For example, even only when the driver recognizes all the situations around the vehicle (step S730), it may be determined that the driver is able to operate the vehicle in the manual driving mode.

In another exemplary embodiment, another step may be added to determine whether the vehicle is operable in the manual driving mode.

Figure 8:
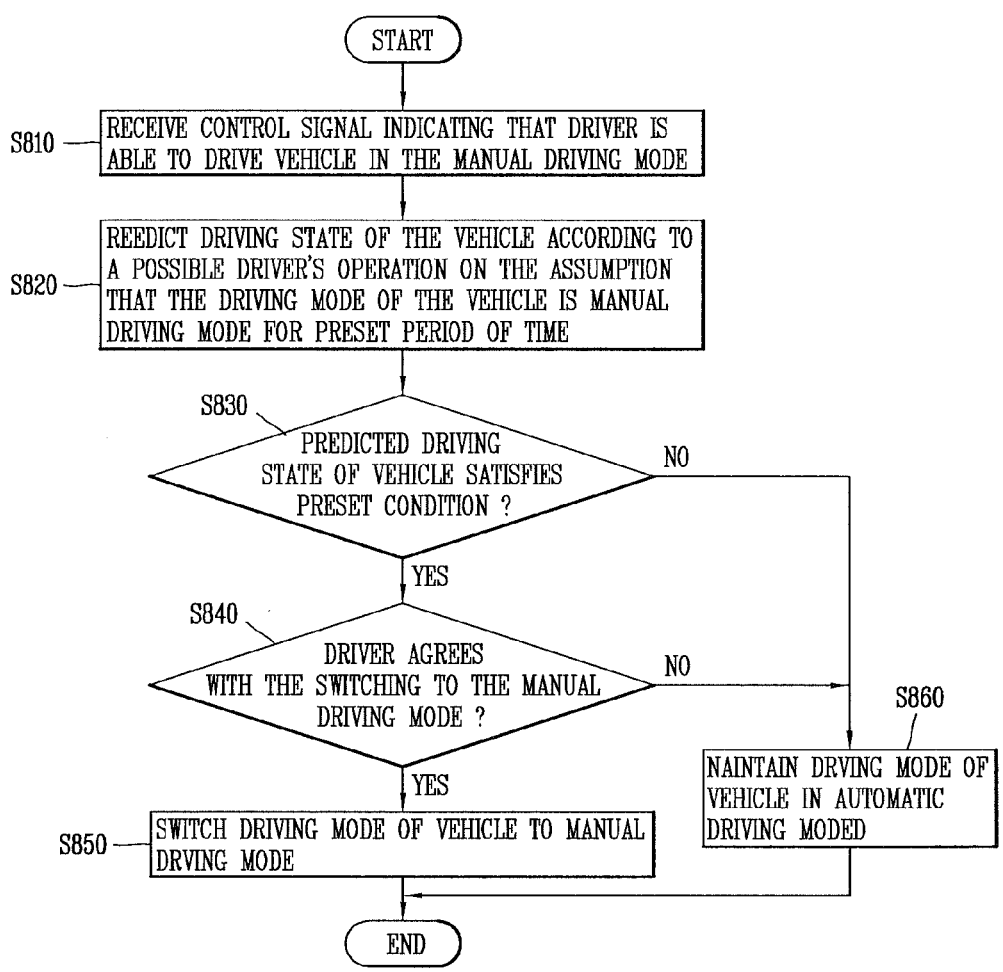
FIG. 8 is a flow chart illustrating an embodiment of switching a driving mode of a vehicle.

FIG. 8 is a flow chart illustrating an embodiment of switching a driving mode of a vehicle.

That is, FIG. 8 is a specific embodiment of steps S530 and S540 of FIG. 5, and each step is executed by the driving state predicting unit 440 and the control unit 450.

Referring to FIG. 8, first, a control signal indicating whether the driver is able to drive the vehicle in the manual driving mode, generated by the operation availability detecting unit 430 is received in step S810.

Next, a driving state of the vehicle according to a possible driver's operation on the assumption that the driving mode of the vehicle is a manual driving mode for a preset period of time is predicted in step S820.

In detail, the driving mode of the vehicle is not actually switched to the manual driving mode, but a driving state of the vehicle on the assumption that the vehicle is operated through driver's inputting such as a driver's operation of the handle, brake, or accelerator for a preset period of time, is predicted.

Thereafter, it is determined whether the predicted driving state of the vehicle meets a preset condition in step S830.

In detail, the preset condition may be set to a condition in which the vehicle is not interfered with by a neighbor vehicle, a pedestrian, an obstacle, and the like, and the vehicle is operated, while keeping his or her lane and observing traffic signals. For example, in step S830, it may be determined whether the driving state of the vehicle predicted in step S820 is that the vehicle is not interfered with by a neighbor vehicle, a pedestrian, an obstacle, and the like, and the vehicle is operated, while keeping its lane and observing traffic signals.

When it is determined that the predicted driving state of the vehicle does not meet the preset condition in step S830, the driving mode of the vehicle is maintained in the automatic driving mode in step S860.

Meanwhile, when it is determined that the predicted driving state of the vehicle meets the preset condition in step S830, the driver is inquired as to whether he or she agrees with the switching to the manual driving mode in step S840.

In an exemplary embodiment, a message window inquiring whether the driver agrees with switching to the manual driving mode may be output on the display unit 460. Thus, the driver may agree or disagree with the switching to the manual driving mode by applying a touch input to an agreement icon or a cancel/reject icon output on the message window.

When the driver agrees with the switching to the manual driving mode in step S840, the control unit 450 switches the driving mode of the vehicle from the automatic driving mode to the manual driving mode in step S850.

That is, when it is predicted that the vehicle will safely operated and the driver directly confirms the manual driving intention, authority to control the vehicle is given to the driver finally.

Meanwhile, when the driver does not agree with the switching to the manual driving mode in step S840, the driving mode of the vehicle is maintained in the automatic driving mode in step S860.

Hereinafter, step S840 of FIG. 8, that is, an embodiment related to directly inquiring about a mode switching intention of the driver will be described.

Figure 9:
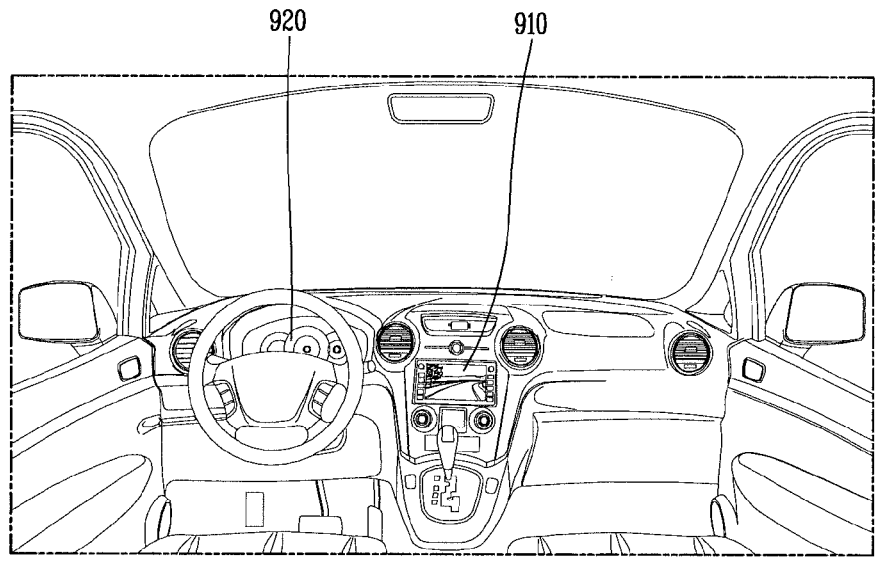
FIG. 9 is a conceptual view illustrating an embodiment in which a display unit of the apparatus for switching a driving mode of a vehicle is positioned according to an exemplary embodiment of the present disclosure.

FIG. 9 is a conceptual view illustrating an embodiment in which a display unit of the apparatus for switching a driving mode of a vehicle is positioned according to an exemplary embodiment of the present disclosure.

Referring to FIG. 9, the display unit 460 of the apparatus 400 for switching a driving mode of a vehicle according to an exemplary embodiment of the present disclosure, the display unit 460 may be disposed in a certain position within a vehicle and output image information (visual information). For example, the display unit 460 may output visual information such as a road guidance screen, a location of a vehicle during parking, a speed of the vehicle during operation, information such as a time, weather, and the like, schedule information, information regarding music being played, a music play control screen, a control screen for adjusting an air-conditioner or a heater (air-conditioning control screen0, and the like.

In an exemplary embodiment, the display unit 460 may be positioned in the center of the dashboard of the vehicle, and may be disposed in a region of a center fascia 910 as a control panel board or a dashboard 920 present between the driver's seat and a passenger seat.

Figure 10:
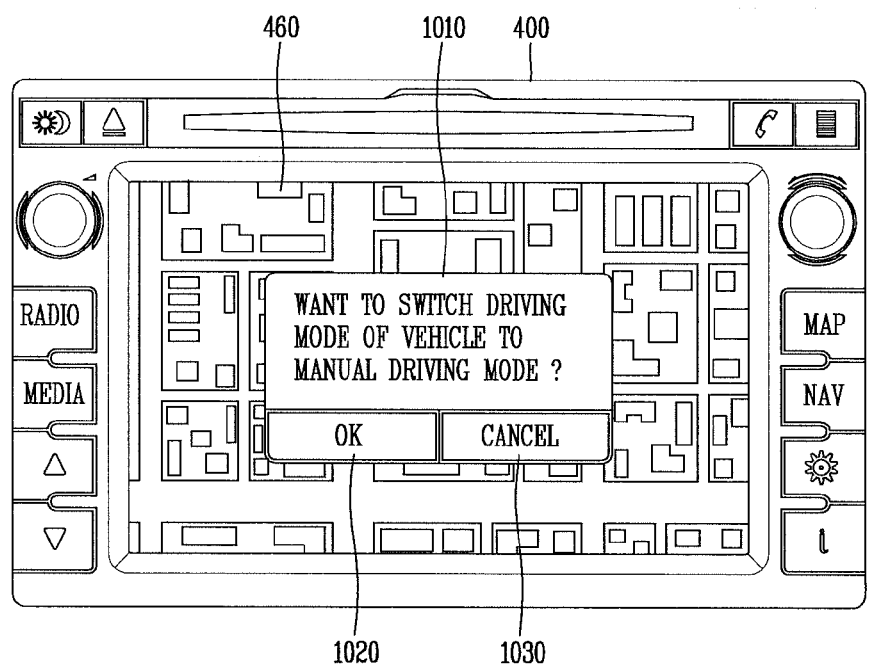
FIG. 10 is a conceptual view illustrating an embodiment for directly confirming an intention to switch to a manual driving mode.

FIG. 10 is a conceptual view illustrating an embodiment for directly confirming an intention to switch to a manual driving mode.

Referring to FIG. 10, a message window 1010 asking whether to switch the driving mode of the vehicle to the manual driving mode may be output on the display unit 460 of the apparatus 400 for switching a driving mode of a vehicle according to an exemplary embodiment of the present disclosure. Here, a confirmation icon 1020 for agreeing with switching to the manual driving mode and a cancel icon 1030 for disagreeing with the switching to the manual driving mode may be output on the messages window 1010.

In an exemplary embodiment, when the driver applies a touch input to the confirmation icon 1020, the driving mode of the vehicle may be switched from the automatic driving mode to the manual driving mode. Meanwhile, when the driver applies a touch input to the cancel icon 1030, the driving mode of the vehicle may be maintained in the automatic driving mode.

That is, in step S840 of FIG. 8, the message window 1010 described above with reference to FIG. 10 may be output.

The apparatus for switching a driving mode of a vehicle and the method thereof according to an exemplary embodiment of the present disclosure has the following advantages.

According to at least one of the exemplary embodiments of the present disclosure, even though a control command for switching a mode is not directly input from a driver, a mode switching intention of the driver may be automatically detected.

Also, according to at least one of the exemplary embodiments of the present disclosure, whether to switch a driving mode may be determined by determining whether the vehicle is able to be safely operated when switched to the manual driving mode.

As a result, a problem arising as a control command for switching a driving mode is input against the driver's intention may be solved. For example, a problem in which the driving mode is switched even when the driver presses a driving mode switching button or inputs a voice control command by mistake, may be solved.

The foregoing embodiments and advantages are merely exemplary and are not to be considered as limiting the present disclosure. The present teachings can be readily applied to other types of apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be considered broadly within its scope as defined in the appended claims, and therefore all changes and modifications that fall within the metes and bounds of the claims, or equivalents of such metes and bounds are therefore intended to be embraced by the appended claims.

What is claimed is:

1. An apparatus configured to switch a driving mode of a vehicle comprising:
   a sensing unit, implemented by at least one processor, configured to sense a state of a driver of a vehicle that is configured to be driven automatically or manually;
   a intention detecting unit, implemented by at least one processor, configured to detect whether or not the driver intends to switch a driving mode of the vehicle from an automatic driving mode to a manual driving mode based on the state of the driver sensed by the sensing unit when the vehicle is being driven in the automatic driving mode;
   an operation detecting unit, implemented by at least one processor, configured to detect whether the driver is able to operate the vehicle in the manual driving mode using the state of the driver sensed by the sensing unit based on the intention detecting unit detecting that the driver intends to switch a driving mode of the vehicle from the automatic driving mode to the manual driving mode;
   a driving state predicting unit, implemented by at least one processor, configured to predict a driving state of the vehicle according to manual driver operation in the manual driving mode for a preset period of time based on the operation detecting unit detecting that the driver is able to operate the vehicle in the manual driving mode; and
   a control unit, implemented by at least one processor, configured to determine whether the predicted driving state of the vehicle meets a preset condition and switch the driving mode of the vehicle from the automatic driving mode to the manual driving mode based on a determination that the predicted driving state of the vehicle meets the preset condition.

2. The apparatus of claim 1, wherein the sensing unit is configured to sense at least one of a position of both hands or both feet of the driver, the driver's posture, the driver's eyes, a degree of blinking of the driver, or a degree to which the driver's eyelids cover the eyes.

3. The apparatus of claim 2, wherein the intention detecting unit is configured to detect that the driver intends to switch a driving mode of the vehicle from the automatic driving mode to the manual driving mode based on the sensing unit sensing that at least one hand of the driver is holding the steering wheel in the automatic driving mode.

4. The apparatus of claim 2, wherein the intention detecting unit is configured to detect that the driver intends to switch a driving mode of the vehicle from the automatic driving mode to the manual driving mode based on the sensing unit sensing that at least one foot of the driver is laid on an accelerator or a brake in a situation in which the vehicle is in the automatic driving mode and a speed is required to be controlled.

5. The apparatus of claim 2, further comprising:
a display unit, implemented by at least one processor, configured to output an object corresponding to a driving mode of the vehicle.

6. The apparatus of claim 5, wherein the operation detecting unit is configured to detect that the driver is able to operate the vehicle in the manual driving mode based on the sensing unit sensing that the driver's eyes are looking toward a preset object output on the display unit or a particular object recognized by an advanced driving assist system (ADAS).

7. The apparatus of claim 6, wherein the preset object includes an object that informs the driver about a dangerous situation around the vehicle based on the vehicle being operated in the manual driving mode.

8. The apparatus of claim 2, wherein the sensing unit is configured to sense the driver's eye gaze, and wherein the operation detecting unit is configured to determine whether a degree to which the sensed eye gaze aligns with a driving route of the vehicle meets a threshold degree and determine that the driver is able to operate the vehicle in the manual driving mode based on a determination that the degree to which the sensed eye gaze aligns with the driving route of the vehicle meets the threshold degree.

9. The apparatus of claim 2, wherein the operation detecting unit is configured to calculate a degree of fatigue of the driver based on a degree of the driver's blinking and a degree to which the driver's eyelids cover the eyes, determine whether the calculated degree of fatigue of the driver meets a threshold degree, and detect that the driver is able to operate the vehicle in the manual driving mode based on a determination that the calculated degree of fatigue of the driver meets the threshold degree.

10. The apparatus of claim 1, wherein the control unit is configured to maintain the driving mode of the vehicle in the automatic driving mode based on a determination that the predicted driving state of the vehicle does not meet the preset condition.

11. The apparatus of claim 1, further comprising a display unit implemented by at least one processor,
wherein the control unit is further configured to:
output, on the display unit and based on the determination that the predicted driving state of the vehicle meets the preset condition, a message window inquiring whether the driver of the vehicle agrees with switching the driving mode of the vehicle from the automatic driving mode to the manual driving mode;
receive an indication that the driver agrees with switching the driving mode of the vehicle from the automatic driving mode to the manual driving mode; and
based on receiving the indication that the driver agrees with switching the driving mode of the vehicle from the automatic driving mode to the manual driving mode, switch the driving mode of the vehicle from the automatic driving mode to the manual driving mode.

12. A method for switching a driving mode of a vehicle configured to be driven automatically or manually, the method comprising:
sensing, by a sensing unit, a state of a driver of a vehicle that is configured to be driven automatically or manually;
detecting whether or not the driver intends to switch a driving mode of the vehicle from an automatic driving mode to a manual driving mode based on the state of the driver sensed by the sensing unit when the vehicle is being driven in the automatic driving mode;
detecting whether the driver is able to operate the vehicle in the manual driving mode using the state of the driver sensed by the sensing unit based on detecting that the driver intends to switch a driving mode of the vehicle from the automatic driving mode to the manual driving mode;
predicting a driving state of the vehicle according to manual driver operation in the manual driving mode for a preset period of time based on detecting that the driver is able to operate the vehicle in the manual driving mode;
determining, by a control unit, whether the predicted driving state of the vehicle meets a preset condition; and
switching, by the control unit, the driving mode of the vehicle from the automatic driving mode to the manual driving mode based on a determination that the predicted driving state of the vehicle meets the preset condition.

13. The method of claim 12, wherein sensing the state of the driver of the vehicle comprises sensing at least one of a position of both hands or both feet of the driver, the driver's posture, the driver's eyes, a degree of blinking of the driver, or a degree to which the driver's eyelids cover the eyes.

14. The method of claim 13, wherein detecting whether or not the driver intends to switch a driving mode of the vehicle from the automatic driving mode to the manual driving mode comprises detecting that the driver intends to switch a driving mode of the vehicle from the automatic driving mode to the manual driving mode based on the sensing unit sensing that at least one hand of the driver is holding the steering wheel in the automatic driving mode.

15. The method of claim 13, wherein detecting whether or not the driver intends to switch a driving mode of the vehicle from the automatic driving mode to the manual driving mode comprises detecting that the driver intends to switch a driving mode of the vehicle from the automatic driving mode to the manual driving mode based on the sensing unit sensing that at least one foot of the driver is laid on an accelerator or a brake in a situation in which the vehicle is in the automatic driving mode and a speed is required to be controlled.

16. The method of claim 13, further comprising:
outputting, on a display unit, an object corresponding to a driving mode of the vehicle.

17. The method of claim 16, wherein detecting whether the driver is able to operate the vehicle in the manual driving mode comprises detecting that the driver is able to operate the vehicle in the manual driving mode based on the sensing unit sensing that the driver's eyes are looking toward a preset object output on the display unit or a particular object recognized by an advanced driving assist system (ADAS).

18. The method of claim 17, wherein the preset object includes an object that informs the driver about a dangerous situation around the vehicle based on the vehicle being operated in the manual driving mode.

19. The method of claim 13, wherein sensing the state of the driver of the vehicle comprises sensing the driver's eye gaze, and wherein detecting whether the driver is able to operate the vehicle in the manual driving mode comprises determining whether a degree to which the sensed eye gaze aligns with a driving route of the vehicle meets a threshold degree and determining that the driver is able to operate the vehicle in the manual driving mode based on a determination that the degree to which the sensed eye gaze aligns with the driving route of the vehicle meets the threshold degree.

20. The method of claim 13, wherein detecting whether the driver is able to operate the vehicle in the manual driving mode comprises calculating a degree of fatigue of the driver based on a degree of the driver's blinking and a degree to which the driver's eyelids cover the eyes, determining whether the calculated degree of fatigue of the driver meets a threshold degree, and detecting that the driver is able to operate the vehicle in the manual driving mode based on a determination that the calculated degree of fatigue of the driver meets the threshold degree.

21. The method of claim 12, further comprising maintaining the driving mode of the vehicle in the automatic driving mode based on a determination that the predicted driving state of the vehicle does not meet the preset condition.

22. The method of claim 12, further comprising:
outputting, on a display unit of the vehicle and based on the determination that the predicted driving state of the vehicle meets the preset condition, a message window inquiring whether the driver of the vehicle agrees with switching the driving mode of the vehicle from the automatic driving mode to the manual driving mode;
receiving, by the control unit, an indication that the driver agrees with switching the driving mode of the vehicle from the automatic driving mode to the manual driving mode; and
based on receiving the indication that the driver agrees with switching the driving mode of the vehicle from the automatic driving mode to the manual driving mode, switching, by the control unit, the driving mode of the vehicle from the automatic driving mode to the manual driving mode.

* * * * *